United States Patent [19]
Bowden

[11] Patent Number: 5,874,650
[45] Date of Patent: Feb. 23, 1999

[54] PROCESS FOR PREPARING 4,4,4-TRICHLOROBUTAN-1-OL

[75] Inventor: Martin Charles Bowden, Huddersfield, United Kingdom

[73] Assignee: Zeneca Limited, London, England

[21] Appl. No.: 889,233

[22] Filed: Jul. 8, 1997

[30] Foreign Application Priority Data

Aug. 7, 1996 [GB] United Kingdom .................... 9614322

[51] Int. Cl.$^6$ .................................................. C07C 29/00
[52] U.S. Cl. ............................................ 568/850; 568/841
[58] Field of Search ..................................... 568/841, 850

[56] References Cited

FOREIGN PATENT DOCUMENTS 1549691  8/1979  Japan .
1017978  1/1966  United Kingdom .

OTHER PUBLICATIONS

Ameduri and Boutevin, "Synthesis of Chlorinated Telechelic Oligomers"—*Macromolecules*, vol. 24:9, 1991, pp. 2475–2484.

Chen et al., "Rearrangements and Conformations of Chloroalkyl Radicals by Electron Spin Resonance"—*J. American Chem. Soc.*, vol. 96:7, 1974, pp. 2201–2208.

Imai et al., "Ring Opening Alkylation of Cyclic Ethers with α–Halogenoalkyllithiums in the Presence of Boron Trifluoride—Dithyl Ether", *J. Chem. Soc., Chem Commun.*, 1994, pp. 2353–2354.

*Primary Examiner*—Michael L. Shippen
*Attorney, Agent, or Firm*—Dianne Burkhard

[57] ABSTRACT

A process for the preparation of 4,4,4-trichlorobutan-1-ol which comprises reacting allyl alcohol with chloroform in the presence of a radical initiator. Preferably the allyl alcohol is added incrementally to the chloroform over the period of the reaction.

9 Claims, No Drawings

PROCESS FOR PREPARING 4,4,4-TRICHLOROBUTAN-1-OL

The present invention relates to an improved process for preparing 4,4,4-trichlorobutan-1-ol by reacting allyl alcohol with chloroform. 4,4,4-Trichlorobutan-1-ol is an important intermediate and product in the chemical industry.

The reaction scheme for this process is as follows

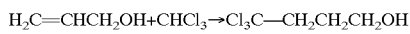

allyl alcohol chloroform 4,4,4-trichlorobutan-1-ol

Preferably the process is carried out in the presence of an radical initiator, with addition of the allyl alcohol to the chloroform over the period of the reaction so that the chloroform is always present in excess of the molar requirement.

According to the present invention there is provided a process for the preparation of 4,4,4-trichlorobutan-1-ol comprising reacting allyl alcohol with chloroform in the presence of at least one radical initiator, characterised by the incremental addition of the allyl alcohol to the chloroform over the period of the reaction. The term "incremental addition" as used herein includes both addition of separate aliquots and also a continuous stream of allyl alcohol.

We have found that surprisingly the process of the present invention provides a satisfactory yield of the 4,4,4-trichlorobutan-1-ol without significant co-production of by-products, particularly oligomeric by-products.

In one preferred embodiment of the present invention, the allyl alcohol may added to the reaction mixture in more two more aliquots over the period of the reaction. Preferably there are three or more additions of the allyl alcohol, more preferably four or more additions, even more preferably eight or more additions. Nevertheless significant yield benefits may be obtained with less than eight separate additions It will be appreciated that the allyl alcohol can be added at either regular or non-regular intervals, and it is not necessary that the same amount of allyl alcohol be added each time. The addition of the second and subsequent aliquots preferably takes place after intervals of at least one hour following the previous addition.

In an especially preferred embodiment of the present invention, the allyl alcohol is continuously fed to the reaction mixture at a controlled rate. This can conveniently be achieved using pump feeding equipment. The rate of addition may be varied over the course of the reaction which may be monitored by sampling and determining the rate of formation of the desired product by the use of gas chromatography.

Preferably, the chloroform is always present present in excess with the overall molar ratio of allyl alcohol to chloroform being less than one. Preferably the overall molar ratio of allyl alcohol to chloroform is at least 1:5, even more preferably it is within the range 1:10 to 1:15.

The reaction is preferably conducted at elevated pressure, preferably in the range of about 80 psi to about 90 psi. The reaction can be conveniently conducted in a pressure reactor. The reaction is also preferably carried out at elevated temperature, preferably within a temperature range of 100°–150° C., and a temperature of about 120°–135° C. is particularly preferred. The pressure may be applied to the contents of the vessel by introducing pressurised inert gas or may be generated within the vessel as a result of heating the contents (autogenic pressure).

Many radical initiators are known and any conveient radical initiator may be used. Preferred initiators include organic peroxides such as diacyl peroxides, eg benzoyl peroxide, and dialkyl peroxides, eg. t-butyl peroxide (TPO), peresters, eg t-butyl perbenzoate, and azo compounds, eg azobisisobutyronitrile (AIBN). Particularly favourable results may be obtained when a peroxide and an azo compound, eg TPO and AIBN, are used in combination. All the initiator(s) may be added to the chloroform at the start of the process, or may also be added in a incremental manner, preferably in admixture with the allyl alcohol.

The performance of the process is also assisted by the presence of a base, preferably a weak base, such as a alkali or alkaline earth metal carbonate or bicarbonate or an alkali metal or alkaline earth metal salt of a C1 to C20 carboxylic acid, such as acetic acid, butyic acid, stearic acid and the like.

The period of the reaction may extend from a about 3 hours to about 48 hours, depending upon the volume of reactants and the temperature and pressure used. Generally a period of from about 5 to about 15 hours is sufficient.

Various further preferred features and embodiments of the present invention will now be described with reference to the following non-limiting examples:

EXAMPLE 1

This Example illustrates the preparation of 4,4,4-trichlorobutan-1-ol in accordance with the process of the present invention The details of the reactants are set out below in Table 1:

TABLE 1

| Material | Weight (g) | Strength (%) | 100% wt | Mol. Wt | mMole | Mole ratio |
|---|---|---|---|---|---|---|
| Allyl alcohol | 3.63 | 99 | 3.59 | 58 | 62 | 1 |
| Chloroform | 82.0 | 99 | 81.1 | 119 | 679 | 11 |
| Sodium acetate | 0.43 | 99 | 0.43 | 82 | 5 | 0.1 |
| PhCO2OtBu | 1.2 | 98 | 1.2 | 194 | 6 | 0.1 |

Chloroform (82 g) and sodium acetate (0.43 g) were charged to a nitrogen purged 100 ml Hasteloy C Parr pressure reactor, and the mixture was heated with agitation to 120° C. A solution of t-butyl perbenzoate (1.2 g) in allyl alcohol (3.6 g) was added in aliquots (ca. 0.5 ml/0.5 hr) via HPLC pump. Complete addition is effected over 6 hr, maintaining the temperature at 120° C., and the mixture is then stirred at 120° c. for a further 2 hr. The reaction is allowed to cool to ambient overnight, filtered and concentrated by rotary evaporation to give the product (8.2 g, 46% yield).

$^1$Hnmr (CDCl$_3$): 2.00–2.15 (m, 2H, CH2), 2.20 (br, 1H, OH, 2.80–290 (m, 2H, CH2CCl3), 3.75 (t, 2H, CH2OH), GCMS: 123 (M$^+$—OH,Cl), 110, 75, 44.

IR: 3350.

EXAMPLE 2

This Example illustrates the process of the invention using continuous addition of the allyl alcohol.

A mixture of chloroform (3576 g) and sodium acetate (17.7 g) was charged to a stainless steel pressure reactor fitted with an agitator and the mixture stirred under autogenic pressure at 115° C. whilst amixture of allyl alcohol (77.5 g) and t-butyl peroxybenzoate (26.0 g) was introduced slowly over a period of 7.5 hours as a continuous stream via an HPLC pump. After completion of the addition the reactor contents were cooled to the ambient temperature and after 15 hours the reactor was vented, the contents heated under autogenic pressure to 115° C. A second aliquot of the mixture of allyl alcohol (77.5 g) and t-butyl peroxybenzoate (26.0 g) was introduced slowly over a period of 7.5 hours as a continuous stream via an HPLC pump. After completion of the second addition the reactor contents were cooled to the ambient temperature and discharged into a still and excess chloroform (ca. 60% v/v of the total) distilled off at atmospheric pressure. The residual mixture was washed with a mixture of 10% w/v sodium bisulfite solution (200 ml) and brine (100 ml), followed by 10% w/v sodium carbonate solution (200 ml) and finally brine (10 ml). The organic phase was separated and dried over anhydrous magnesiun sulfate, filtered and concentrated under reduced pressure to remove the more volatile components to give a mobile yellow oil (450.2 g) comprising 54% 4,4,4-trichlorobutan-1-ol (yield 51% with respect to allyl alcohol) in admixture with unreacted allyl alcohol.

I claim:

1. A process for the preparation of 4,4,4-trichlorobutan-1-ol comprising reacting allyl alcohol with chloroform in the presence of a radical initiator, characterized by conducting the reaction in the presence of a base selected from alkali metal carbonates, alkali metal bicarbonates and alkali metal salts of carboxylic acids and by the incremental addition of the allyl alcohol to the chloroform.

2. A process according to or claim 1 wherein the incremental addition is achieved by the addition of separate aliquots of allyl alcohol over the period of the reaction.

3. A process according to claim 1 wherein the incremental addition is achieved by the continuous addition of the allyl alcohol to the chloroform over the period of the reaction.

4. A process according to claim 1 conducted under elevated pressure and elevated temperature conditions.

5. A process according to claim 4 conducted at a pressure within the range 80 to 90 psi.

6. A process according to claim 4 conducted at a temperature within the range 100°–150° C.

7. A process according to claim 1 wherein the radical initiator is selected from an organic peroxide or perester and an azo compound.

8. A process according to claim 7 wherein the radical initiator is selected from t-butyl perbenzoate, t-butyl peroxide, azobisisobutyronitrile and a mixture thereof.

9. A process according to claim 1 wherein the overall molar ratio of chloroform to allyl alcohol is within the range 10:1 to 15:1.

* * * * *